United States Patent
Worley

(10) Patent No.: US 7,959,587 B2
(45) Date of Patent: *Jun. 14, 2011

(54) PORTABLE ELECTRONIC SOUND, PHYSIOACOUSTIC, AND COLORED LIGHT THERAPY SYSTEM

(76) Inventor: August John Worley, Asheville, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 12/437,247

(22) Filed: May 7, 2009

(65) Prior Publication Data

US 2009/0275794 A1    Nov. 5, 2009

Related U.S. Application Data

(63) Continuation of application No. 11/317,112, filed on Dec. 23, 2005, now Pat. No. 7,537,576.

(51) Int. Cl.
*A61H 1/00* (2006.01)
(52) U.S. Cl. ............................................ 601/46; 601/47
(58) Field of Classification Search ............... 601/46–47, 601/49; 84/600, 706, 723
See application file for complete search history.

(56) References Cited

U.S. PATENT DOCUMENTS

| | | | | |
|---|---|---|---|---|
| 3,529,070 A | * | 9/1970 | Jones | 84/639 |
| 4,375,287 A | * | 3/1983 | Smith | 463/22 |
| 7,537,576 B1 | * | 5/2009 | Worley, III | 601/46 |
| 2001/0039869 A1 | * | 11/2001 | Oren-Chazon | 84/1 |

* cited by examiner

*Primary Examiner* — Michael A. Brown
(74) *Attorney, Agent, or Firm* — IP Strategies

(57) ABSTRACT

The present invention is a portable integrated sound, physioacoustic, and colored light apparatus. This is a self-contained electrically powered device designed to stimulate and facilitate the human body's innate self-healing mechanisms. The active components are housed in a portable pyramidal-shaped lower enclosure (100) with a single recessed panel (102) on one side of the unit containing a user interface for controlling the pitch and tonal quality of the generated sound and physioacoustic frequencies. The unit also contains specified colored light elements situated under a quartz crystal pyramid capstone (108) which react with the sound frequencies by increasing and decreasing in intensity. The user or therapist has the capability to access the electronically generated sound source to achieve a wide variety of tonal sound and vibrational components, as well as the ability to select the desired colored light therapy component.

19 Claims, 4 Drawing Sheets

PORTABLE ELECTRONIC SOUND, PHYSIOACOUSTIC, AND COLORED LIGHT THERAPY SYSTEM

CROSS-REFERENCE TO RELATED APPLICATIONS

This application claims the benefit of provisional patent Ser. No. 60/639,460, filed 2004 Dec. 23 by the present inventor.

FEDERALLY SPONSORED RESEARCH

Not Applicable

SEQUENCE LISTING OR PROGRAM

Not Applicable

BACKGROUND OF THE INVENTION

1. Filed of Invention

This invention relates to an integrated sound, physioacoustic, and colored light apparatus; particularly to a portable, user-controlled unified system device.

2. Prior Art

Sound directs matter and thus anything that exists in the current physical reality can be directly and profoundly influenced by sound. The human DNA functions within a specific pattern of frequencies and these frequencies direct all of the physical body's processes and thus the type and range of perception that can be physically experienced. This is of paramount importance to maintaining a healthy human body. If one can direct human perception and experience through sound manipulation, it can heal physically as well as emotionally. Therefore, the manipulation of sound frequencies of a specific nature and manner can create resonances, implications, and other direct triggers to the human physical system which will manifest in the form of physical (and non-physical) experiences.

For centuries, mechanical toning apparatus has been used to achieve a stable toned sound towards this end. Tibetan monks have used large resonant "singing" bowls as part of their meditative practice, creating simple yet profoundly powerful harmonic structures as part of their daily meditations and as a pathway to spiritual enlightenment and superior health. Australian Aboriginal peoples have used a wind device known as a didgeridoo as part of their spiritual and healing practice since before recorded history. Unfortunately, mechanical toning devices such as these must be continually stimulated in some participatory way to generate sound.

In recent history, the only devices capable of generating stable, continual, and listenable physically supportive sounds were musical instruments such as synthesizers. However, they too must be manipulated to a high degree in order to create their sound, and most of them do not have the capability to project the developed sound without an external means of amplification.

In addition, there is a performance aspect to a musical instrument such as a synthesizer, which many non-musicians find highly intimidating. A set of piano keys placed in front of a person produces a degree of expectation of being able to competently operate the musical appliance with an intention to produce sound in the form of music and to entertain.

Further, the other functional aspect of sound utilized as a sensory modulation technique other than the audible component is the vibrational or physical component. This component is primarily effective to the human body as a vibrational modality only at the lower end of the frequency spectrum, typically at or below 150 Hz. The practice of implementing sound expressly as a vibrational stimulation technique is a newly developed science known as "physioacoustics".

Physioacoustics is a scientific method of applying low frequency stimulation to the human body in such a way as to obtain desired emotional or physical effects. Physioacoustics may be thought of as the science that takes the active ingredients out of music, concentrates them, and infuses them in pure form to motivate or heal.

The delivery system must be considered when imparting the created sound for it to be experienced by the listener, or in the case as a sensory modulation technique in physioacoustic therapy. Several types of delivery systems have been proposed—for example, a chair, as disclosed in U.S. patent US200100260.87A1 to Tomita (2001) or a bed apparatus as disclosed in European Patent EP0417388A2 to Komatsu (1991) have been used with a similarly associated objective. However, these technologies are only intended to reproduce pre-recorded sound and do not incorporate the capability for the user to generate and develop the sound. Another disadvantage of these technologies is that the apparatus is large and unwieldy, so that the placement of the apparatus is essentially a permanent installation.

An addressed portable application was proposed, for example in U.S. patent US20050015027A1 by Kojima (2005) describing a vibrating cushion. Although portable, this is another example of a recorded sound reproduction apparatus, affording the user no real-time continuous control over the content of the source information. The property of incorporating colored light therapy is not addressed by this invention.

The use of ambient colored light may be incorporated into the use of sound as a sensory modifying and healing modality. The practice of applying colored light therapy (Phototherapy), is known to have come into being over one hundred years ago, beginning with Swedish physician Dr. Niels Finsen's work in 1893 for the treatment of smallpox utilizing red light. Ongoing research in the application of other colors of visible light continue to be used in the treatment of painful joints, skin burns, headaches, fevers, and emotionally-based problems.

A delivery system has been proposed—for example, WO01/45780A1 to Fenyo (2001) discloses a whole room process and apparatus whereas a colored light apparatus is provided as an associated healing modality together with a sound reproduction apparatus. However, there is no mechanism for reactively associating the sound information with the selected light colour or intensity. This feature is desirable, as the synchronization of the two sensory modalities has a valuable effect towards achieving a synchronic "whole-system" effect conducive to human physiology. Along with that aspect, the apparatus described also shares the disadvantage of being a permanent installation and inherently expensive.

OBJECTS AND ADVANTAGES

Accordingly, several novel objects and advantages of my invention are:
(a) to provide a device capable of electronically generating a stable, continual, and listenable physically supportive sound in a stereophonic format requiring no musical training;
(b) to provide a device which can also utilize the generated sound as a means of physioacoustic stimulation, (c) to provide a means of allowing the user to interface with the sound generating apparatus whereby they may control a wide variety of intrinsic parameters such as pitch, volume, and the tonal characteristics of the generated sound as well as that of the physioacoustic stimulation;

(d) to provide a colored light therapy apparatus which is responsively associated with the generated sound information so as to be experienced as incorporated with the sound;

(e) to provide all of these healing modalities in an attractive, stand-alone, reasonably inexpensive portable enclosure that may be incorporated into already existing human physical support apparatus or furniture.

Further objects and advantages are to provide the user with a programmable free-running timer function allowing the device to function continually and indefinitely automatically generating pitch and associated colour changes until user interaction determines otherwise. This feature would be valuable for integrating the device with other practices or human occupations that require the use of the hands. Still further objects and advantages of my invention will become apparent from a consideration of the drawings and ensuing description.

SUMMARY OF THE INVENTION

The present invention advantageously provides an integrated sound, physioacoustic, and colored light apparatus, and particularly to a portable, user-controlled unified system device. It is intended that the user have the capability to access the electronically generated sound source to achieve a wide variety of tonal sound and vibrational components as well as the ability to select a desired colored light therapy component.

This interactive aspect of the present invention is superior to existing recorded sound or music reproducing apparatus.

Furthermore, by providing all of these healing and sensory modification modalities in a unified portable format, problems associated with fixed installed systems such as high production costs and immovability are eliminated.

DETAILED DESCRIPTION OF THE INVENTION

Figure 1:
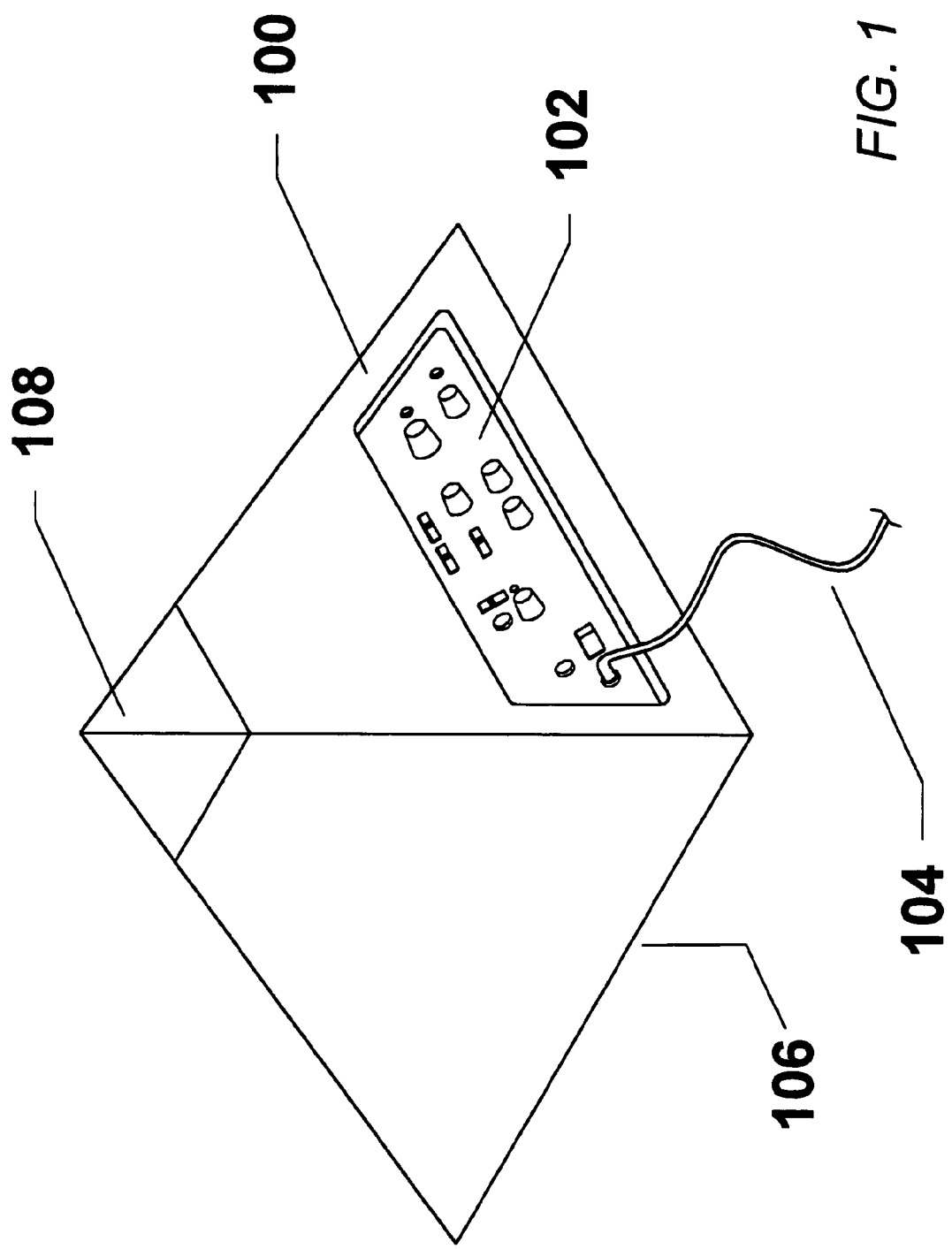
FIG. 1 shows a perspective view of a preferred embodiment of the apparatus of the present invention.
Figure 2:
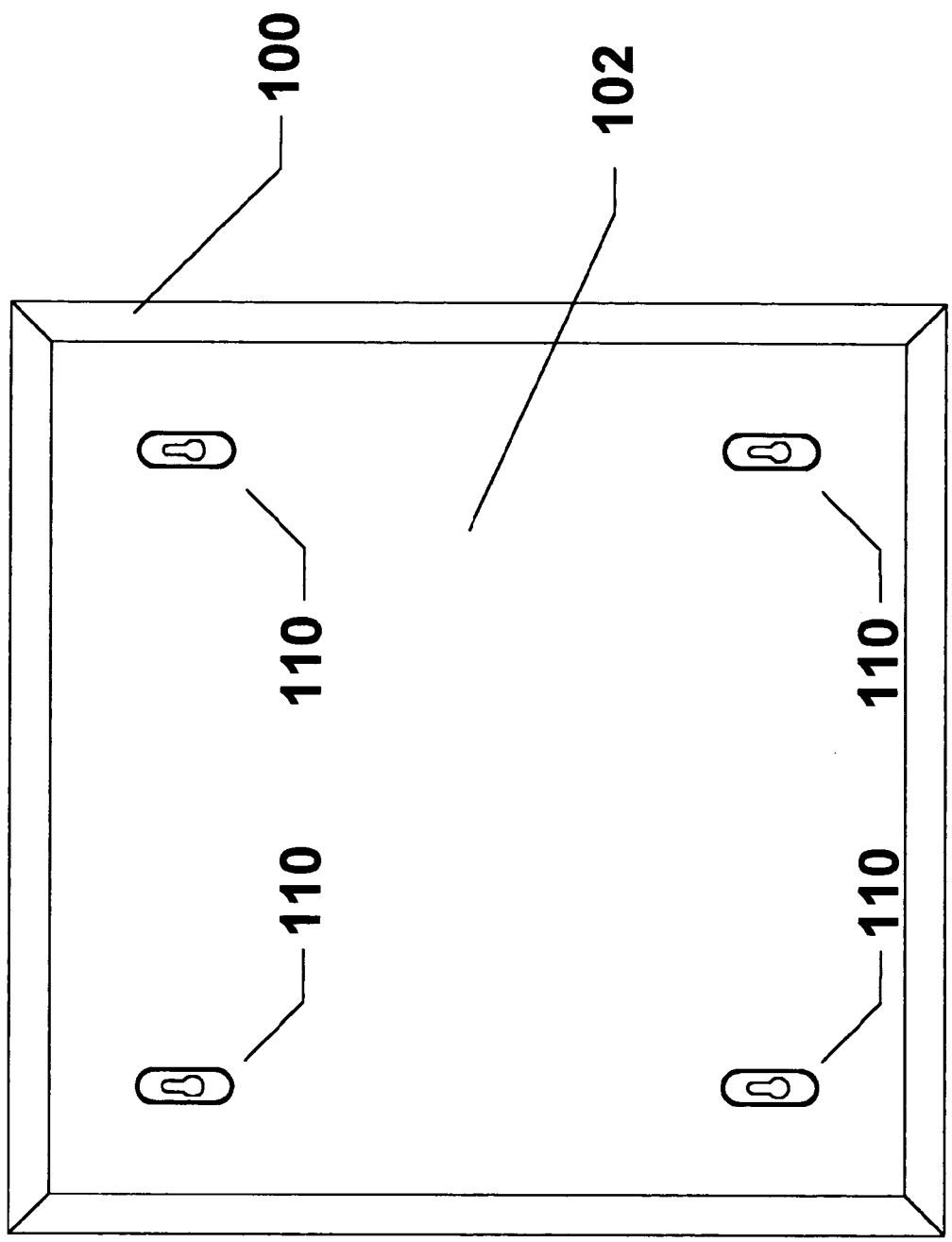
FIG. 2 shows a plan view of the underside of base panel shown in FIG. 1.
Figure 3:
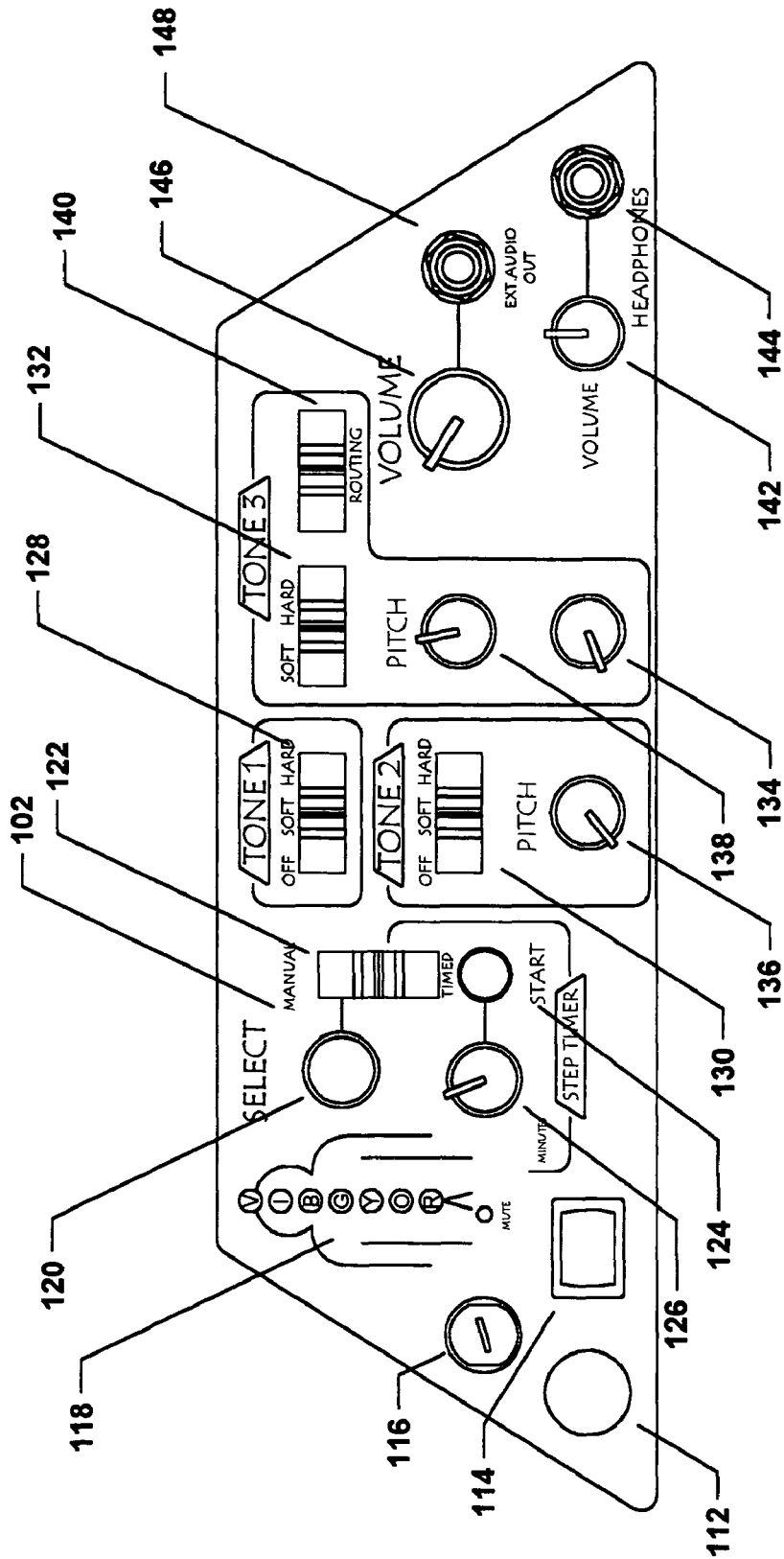
FIG. 3 shows a detail drawing of the front panel elements and user interface controls of FIG. 1.
Figure 4:
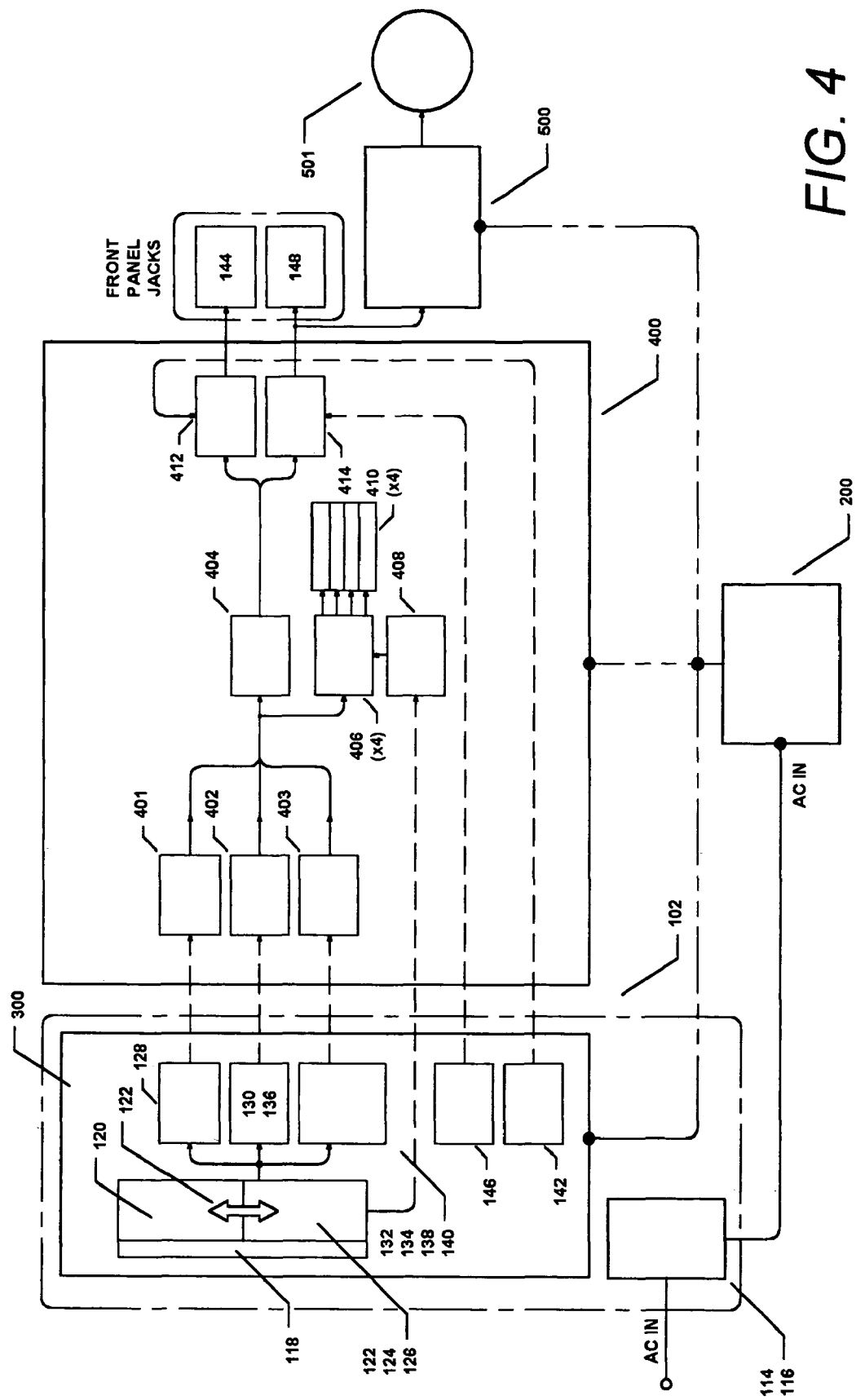
FIG. 4 shows a schematic example of the block diagram of the electronic sound and light generating assembly circuit.

Hereinafter, the preferred embodiments of the novel portable electronic sound, physioacoustic, and colored light therapy system will be described with reference to the accompanying drawings, FIG. 1-4 in detail.

Incidentally, since the embodiments described below are preferred specific examples of the present invention, and although technically preferred various limitations are given, the scope of the present invention is not limited to these embodiments unless there is a description to limit the present invention particularly in the following explanation.

The present invention is a portable, self-contained electrically powered apparatus designed to generate a stable, controllable audible and vibrational sound energy and a corresponding colored light. All electrical components are housed in a pyramidal shaped enclosure structure, approximately 1 foot in height. It is roughly constituted by lower cabinet housing 100, constructed from natural materials such as but not limited to hardwood, with attached base panel 106, of a similar material, creating a sealed resonant chamber. Crystal Capstone 108 is comprised of solid quartz permanently mounted atop the lower cabinet structure, through which the generated light is allowed to project. A single recessed control panel 102 is on one face of the lower cabinet unit. This panel also contains the entry point for the AC supply cord 104. Four mechanically keyed plates 110, 110, 110, 110 are recessed into the base panel.

The control panel 102 is the only control surface located on the structural housing and contains the user interface for controlling the pitch, volume and tonal quality of the generated sound frequencies. The entry point opening 112 for the AC supply cord 104 is also located in the panel, where the unit power switch 114 and accompanying AC supply fuse holder 116 also reside. This connects to the power supply PC Board 200, providing regulated DC supply voltages to the panel PC board 300, main PC board 400, and power amplifier PC board 500.

The pitch and color methodology of the system is based on the classic Eastern philosophy of the existence in the human body of an organization of unseen energetic vortexes called Chakras. Traditionally, each one of these energetic centers has a corresponding musical note frequency and colour frequency associated with it. The colored light aspect of the present invention is designed and organized utilizing this ancient and universally accepted convention.

As a unified, widely accepted platform used to develop and integrate sound and light therapy, the Chakra system is ideal. This system is physically organized in order from lowest to highest as one moves up the human body's spinal column. The corresponding musical note pitch increases in frequency accordingly as does the colour spectrum frequency. The colors are organized in order from lowest to highest as Red, Orange, Yellow, Green, Blue, Indigo, and Violet. This embodiment employs an $8^{th}$ location as a mute location. This display ladder array 118 is depicted by the human figure which is backlit by 8 LEDs.

Pitch control is determined by select button 120, selecting which of the seven available base pitches and its corresponding colour the system will generate. Furthermore, there is a mode slide switch 122, which determines which of the two available pitch/colour selection statuses the unit will operate in, the options being either manual mode or timed modes. The timer start button 124, and the interval length control knob 126, determine the operational parameters when in timed mode.

The Main PC board 400 has three independent voltage controlled tone generators, 401, 402, 403, audio signal mixer 404, colored light display selection circuitry 406, four sets of colored light display driver circuitry 408, each driving a bank of colored LEDs 410, headphone volume control circuitry 410, and output volume control circuitry 412, mounted thereon. The audible output of TONE 1 is selected by slide switch 128. The audible output of TONE 2 is selected by slide switch 130. The audible output of TONE 3 is selected by switch 132. The relative amount of audible output generated by TONE 3 is variable via control knob 134.

Control knob 136 varies the pitch of TONE 2. Control knob 138 varies the pitch of TONE 3. Slide switch 140, selects the routing destination of the waveform developed by the TONE 3 oscillator. Knob 142 controls the volume level amount of the audio appearing at the headphone jack 144. Knob 146 controls the signal volume level at external audio jack 144, and the amount of the audio being sent to the power amplifier PC board 500 which in turn drives the physioacoustic driver 501.

Operation

The device may be operated by placing it on any level surface and applying AC power via the power cord 104. The device will generate sound frequencies and impart the sound energy through physical contact with any associated surface.

A naturally resonant conducive material is most effective for transmitting the sound energy. The four mechanically keyed plates 110, 110, 110, 110 located on the underside of the unit allow attachment to a physical surface such as a floor, wall or massage table. A dimly lit room is recommended to enhance the effect of the colored light apparatus.

A therapist or user switches on power by placing the power switch 114 in the ON position. Applying power to the device instantaneously causes the unit to begin generating a stable tone and corresponding emitted light.

The sound will be heard and felt through the lower cabinet 100, the colored light emitted through the crystal capstone 108. The pitch of each of the tone generators as related to the corresponding color which is displayed on the panel figure 118 to the left of the select switch 120 and also corresponds to the colored light emitted through the crystal capstone 108. The generated stereo sound output is monitored by plugging a set of stereo headphones into the audio jack 144 and adjusting the volume 142.

The generated sound frequency pitch is selected by depressing the select button 120. Each time the select button 120 is depressed, the pitch will increase corresponding to the next highest Chakra setting, moving up one position the array ladder in the order indicated above. When the select button 120 is depressed while the system is at the $7^{th}$ Chakra position, the system will advance to a "mute" position, whereas the sound and emitted light will cease in this location. Depressing the select button 120 once again will start the cycle from the $1^{st}$ Chakra position (Red).

The mode slide switch 122 determines whether the control of the selection process is in either the manual when in the up position, or in the timed mode in the down position. The timed function will override the select button 120, and automatically select the pitch and color at a programmed rate per Chakra location dependent upon the setting of control knob 126. The timer interval is initiated by depressing button 124. The select function also determines which of the four LED 410 colors will activate to create the appropriate resultant color. The colored LEDs 410 situated beneath the crystal capstone 108 respond to the generated sound frequencies by increasing and decreasing in intensity.

The pitch of tone generator 1 401 can be considered the reference pitch and is dedicated to a preset internally tuned pitch for each of the seven Chakra locations outlined above. A wide range of sound qualities are available by combining the three tone generation sources available. Each tone generator each feature a soft and hard tonal quality selectable via switches 128, 130, and 132. The soft tone switch position generates a sound comprised of an odd-order harmonic series and is reminiscent of a singing bowl. The hard tone switch position generates a sound comprised of even and odd-order harmonics and is reminiscent of a bassoon. The generated frequencies are in the 26-555 Hz audio range.

The pitch of tone generator 2 402 is variable and has a control knob 136 for independently varying the pitch of that tone. Full counter-clockwise on this control tunes the pitch to unison with that of the pitch of tone generator 1 401. Full clockwise increases the pitch to about an octave above tone generator 1 401. Tone generator 3 403 functions in the same manner but is tuned an octave higher than tone generator 1 401 and tone generator 2 402 with the control knob 138 turned full CCW, and can be varied up to about 2 and one half octaves above the pitch of tone generator 1 401. This allows adding complex upper harmonic components to the low frequency sound. Rather than have a selectable off position on switch 132, tone generator 3 403 has a volume that is controllable by the amount control knob 134 when in audible mode, full clockwise being the maximum volume.

The routing switch 140 is a mode switch determining whether tone generator 3 403 will function as either an audible tone or as a pitch control frequency for tone generator 1 401 and tone generator 2 402. Repetitive pitch changes may be used to affect the overall sound by using this tone generator as a control source creating interesting pitch change effects. This effect is best described as an "unseen hand" sweeping the pitch up and down in a consistently repetitive manner. When routed as a pitch modulation source the amount of this effect is variable via control knob 134.

This audio signal appearing at the headphone jack 144 is also audibly and vibrationally reproduced within the unit cabinet through the internally mounted physioacoustic driver 501. It has a separate knob 146 for controlling that volume, which also controls the volume of the audio signal appearing at the external audio out jack 148.

All of the controls pertaining to pitch, volume, and tonal quality are continuously variable by the user during operation.

ADVANTAGES

From the description above a number of advantages of the present invention become evident:

(a) By providing all of these healing and sensory modification modalities in a unified portable format, problems associated with fixed installed systems such as high production costs and immovability are eliminated.

(b) Any suitable human support system such as a massage table, floor surface, etc. may be implemented as a vibrational vehicle.

(c) For semi-permanent installations the keyed mechanical hardware on the base of the unit cabinet allow for a removable attachment to any physical surface.

(d) This invention offers those without musical instrument training the possibility of producing sound without the performance aspect inherent in a musical instrument.

(e) The user has the capability to access the electronically generated sound source to achieve a wide variety of tonal sound and vibrational components, as well as the ability to select a desired colored light therapy component. They are able to effect changes in pitch, tonal texture, and volume as they so desire. The immediacy of the interactive aspect of this system is superior to that of a recorded sound or music reproducing apparatus.

(f) The ability to use a active stereo imaged sound of a continual and repetitive nature has been clinically revealed to promote whole brain activation, meditative states of mind and altered states of consciousness.

(g) Low frequency sound of the nature generated by the present invention has been known to cause physiologic and psychological calming, relaxation, relieve anxiety, and promote a sense of well being.

(h) The use of physioacoustic vibration can be applied as a means of stimulating the physical human structure to achieve a massage effect of the organs, lymphatic, and endocrine system, encouraging detoxification.

(i) Physioacoustic sound is a drug-free option for treatment of chronic pain and can ameliorate pain without clouding the mind. The FDA has listed physioacoustic equipment as a Class One medical device and allows the claims of relief of pain, increase of blood circulation, and relaxation.

Conclusion, Ramifications and Scope

Accordingly, the reader will see that the present invention advantageously provides a high quality, portable, and affordable sound, physioacoustic, and colored light apparatus with a high degree of flexibility in application.

Furthermore, the apparatus has additional advantages in that it allows a bodywork health practitioner such as a massage therapist, acupuncturist, or energy healer the capability of integrating additional new healing modalities into their already existing practice;

it provides traditional health care practitioners such as medical doctors the possibility of adding a "relaxation station" to their waiting room to serve those prone to office visit anxiety;

it offers dentists a drug-free, non-toxic option to their clients during their stay in the examination chair by adding the calming properties of sound and colored light to their treatment;

it provides those with no musical training or aptitude the ability to experiment with sound;

Although the description above contains many specificities, these should not be construed as limiting the scope of the invention but as merely providing illustrations of some of the presently preferred embodiments of this invention. For example, the enclosure can have other shapes, such as circular, rectangular, or cubic; the materials may be changed to facilitate production requirements; the control compliment may be altered to include additional features, etc.

Thus the scope of the invention should be determined by the appended claims and their legal equivalents, rather than by the examples given.

The invention claimed is:

1. A portable electronic therapy system, comprising:
   an enclosure;
   a tone generator in the enclosure, said tone generator configured to emit a tone having a frequency selected from a plurality of predetermined frequencies, wherein each predetermined frequency in the plurality of predetermined frequencies is associated with a chakra of the human body; and
   pitch selection means for enabling the frequency of the tone to be set at a predetermined frequency in the plurality of predetermined frequencies;
   wherein the enclosure comprises a control panel;
   wherein the control panel comprises a display ladder array comprising an image of a human figure and an array of lights arranged along the image of the human figure.

2. A portable electronic therapy system according to claim 1, wherein the enclosure comprises a housing comprising a control panel, and the pitch section means is a manual switch on the control panel.

3. A portable electronic therapy system according to claim 1, wherein the system further comprises a timer within the enclosure and the pitch selection means is an automatic switch controlled by the timer.

4. A portable electronic therapy system according to claim 1, wherein the enclosure comprises a housing, a base panel below the housing, and a capstone above the housing.

5. A portable electronic therapy system according to claim 4, wherein the housing and the base panel define a sealed resonant chamber.

6. A portable electronic therapy system according to claim 4, wherein the enclosure is pyramidal.

7. A portable electronic therapy system according to claim 4, wherein the housing comprises a light configured to emit light through the capstone during operation of the system.

8. A portable electronic therapy system according to claim 1, further comprising (1) second and third, tone generators configured to emit tones having frequencies not set by the pitch sections means, and (2) pitch control means for controlling the frequencies of the second and third tone generators.

9. A portable electronic therapy system according to claim 8, wherein the enclosure comprises a control panel and the pitch control means comprises knobs on the control panel.

10. A portable electronic therapy system, comprising:
    an enclosure;
    a tone generator in the enclosure, said tone generator configured to emit a tone having a frequency selected from a plurality of predetermined frequencies, wherein each predetermined frequency in the plurality of predetermined frequencies is associated with a chakra of the human body;
    pitch selection means for enabling the frequency of the tone to be set at a predetermined frequency in the plurality of predetermined frequencies;
    second and third tone generators configured to emit tones having frequencies not set by the pitch sections means; and
    pitch control means for controlling the frequencies of the second and third tone generators.

11. A portable electronic therapy system according to claim 10, wherein the enclosure comprises a control panel.

12. A portable electronic therapy system according to claim 11, wherein the control panel comprises a display ladder array comprising an image of a human figure and an array of lights arranged along the image of the human figure.

13. A portable electronic therapy system according to claim 10, wherein the enclosure comprises a control panel and the pitch control means comprises knobs on the control panel.

14. A portable electronic therapy system according to claim 10, wherein the enclosure comprises a housing comprising a control panel, and the pitch section means is a manual switch on the control panel.

15. A portable electronic therapy system according to claim 10, wherein the system further comprises a timer within the enclosure and the pitch selection means is an automatic switch controlled by the timer.

16. A portable electronic therapy system according to claim 10, wherein the enclosure comprises a housing, a base panel below the housing, and a capstone above the housing.

17. A portable electronic therapy system according to claim 16, wherein the housing and the base panel define a sealed resonant chamber.

18. A portable electronic therapy system according to claim 16, wherein the enclosure is pyramidal.

19. A portable electronic therapy system according to claim 16, wherein the housing comprises a light configured to emit light through the capstone during operation of the system.

* * * * *